(12) United States Patent
Millet (10) Patent No.: US 7,904,258 B2
(45) Date of Patent: Mar. 8, 2011

(54) SYSTEM FOR MEASURING VISCOSITY

(75) Inventor: Frédéric Millet, Paris (FR)

(73) Assignee: Gilson SAS, Villiers-le-Bel (FR)

( * ) Notice: Subject to any disclaimer, the term of this patent is extended or adjusted under 35 U.S.C. 154(b) by 0 days.

(21) Appl. No.: 12/389,061

(22) Filed: Feb. 19, 2009

(65) Prior Publication Data

US 2009/0216465 A1 Aug. 27, 2009

(30) Foreign Application Priority Data

Feb. 21, 2008 (FR) .................................... 08 51120

(51) Int. Cl.
*G01N 11/00* (2006.01)
(52) U.S. Cl. ......................................................... 702/50
(58) Field of Classification Search ...................... 702/50
See application file for complete search history.

(56) References Cited

U.S. PATENT DOCUMENTS

| | | | |
|---|---|---|---|
| 3,193,148 A | 7/1965 | Anthon | |
| 3,640,434 A | 2/1972 | Walker | |
| 3,835,874 A | 9/1974 | Dellasala | |
| 3,990,295 A * | 11/1976 | Renovanz et al. | 73/54.09 |
| 4,554,939 A | 11/1985 | Kern et al. | |
| 4,679,446 A | 7/1987 | Sheehan et al. | |
| 2005/0220676 A1 | 10/2005 | Tran | |

FOREIGN PATENT DOCUMENTS

| | | |
|---|---|---|
| EP | 0608425 A1 | 3/1994 |
| JP | 56164957 | 12/1981 |
| JP | 2007199031 | 8/2007 |
| WO | WO 2006066565 | 6/2006 |
| WO | WO 2007077527 | 7/2007 |

OTHER PUBLICATIONS

International Search Report for PCT/IB2007/000021, mailed on Jan. 6, 2007.
French Preliminary Search Report for FR 0851120, mailed on Oct. 24, 2008.
French Written Opinion on Patentability for FR 0851120, mailed on Feb. 21, 2008.
International Search Report and Written Opinion for PCT/IB2009/000154 mailed Jun. 5, 2009.
International Preliminary Report on Patentability issued in PCT/IB2009/000154 and mailed on Sep. 2, 2010.

* cited by examiner

*Primary Examiner* — Tung S Lau
(74) *Attorney, Agent, or Firm* — Foley & Lardner LLP (57) ABSTRACT

A system for determining a viscosity of a fluid is provided. The system includes an intake chamber, a tube, a piston, an actuator, a sensor, and a processor. The tube communicates with the intake chamber and includes a channel including a cylindrical portion with a constant diameter cross section. The piston is mounted in the intake chamber. The actuator is configured to move the piston within the intake chamber at a constant speed during a time window to regulate a fluid in the cylindrical portion. The sensor is configured to measure a pressure a plurality of times during the time window to define a plurality of pressure measurements. The processor is configured to receive the defined plurality of pressure measurements, to determine a slope associated with the received plurality of pressure measurements, and to determine a viscosity of the fluid based on the determined slope.

23 Claims, 6 Drawing Sheets

SYSTEM FOR MEASURING VISCOSITY

CROSS-REFERENCE TO RELATED APPLICATIONS

This application claims priority under the Paris Convention to French Patent Application No. 08 51120, filed Feb. 21, 2008, the disclosure of which is incorporated by reference in its entirety.

BACKGROUND

Using a pipette, a volume of liquid is aspirated into the pipette. The volume of liquid may then be dispensed in one or more dispensation volumes. A piston drive mechanism controls the aspiration and the dispensation of the liquid in specified volumes by imparting motion to a piston. Motion of the piston is controlled by a thrust exerted by the piston drive mechanism. The pipette may operate in a manual mode wherein the user manually controls the speed and the volume of aspiration or of dispensation of the liquid or in a motorized mode wherein a motor controls the aspiration and/or dispensation of the liquid. Various parameters including a speed, a volume, a number of aspirations, a number of dispensations, etc. may be selected using an input interface. A multi-channel pipetting system includes a multi-channel pipette that includes a plurality of pistons. Pipettes further can be held in the hand of an operator during aspiration and dispensation of the liquid or may be included as part of an automated system.

SUMMARY

In an illustrative embodiment, a system for determining a viscosity of a fluid is provided. The system includes, but is not limited to, an intake chamber, a tube, a piston, an actuator, a sensor, and a processor. The tube communicates with the intake chamber and includes a channel including a cylindrical portion with a constant diameter cross section. The piston is mounted in the intake chamber. The actuator is configured to move the piston within the intake chamber at a constant speed during a time window to regulate a fluid in the cylindrical portion. The sensor is configured to measure a pressure a plurality of times during the time window to define a plurality of pressure measurements. The processor is configured to receive the defined plurality of pressure measurements, to determine a slope associated with the received plurality of pressure measurements, and to determine a viscosity of the fluid based on the determined slope.

In another illustrative embodiment, a method for determining a viscosity of a fluid is provided. A piston mounted in an intake chamber is actuated in a first direction at a first constant speed during a first time window to aspirate a fluid in a cylindrical portion of a channel of a tube. The channel is in communication with the intake chamber. The cylindrical portion has a constant diameter cross section. A pressure is measured a first plurality of times during the first time window to define a first plurality of pressure measurements. A first slope associated with the defined first plurality of pressure measurements is determined. The piston is actuated in a second direction opposite the first direction to dispense a portion of the aspirated fluid from the tube. The piston is actuated in the first direction at a second constant speed during a second time window to aspirate the fluid in the cylindrical portion of the channel of the tube. The pressure is measured a second plurality of times during the second time window to define a second plurality of pressure measurements. A second slope associated with the defined second plurality of pressure measurements is determined. A viscosity of the fluid is determined based on the determined first slope and the determined second slope.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
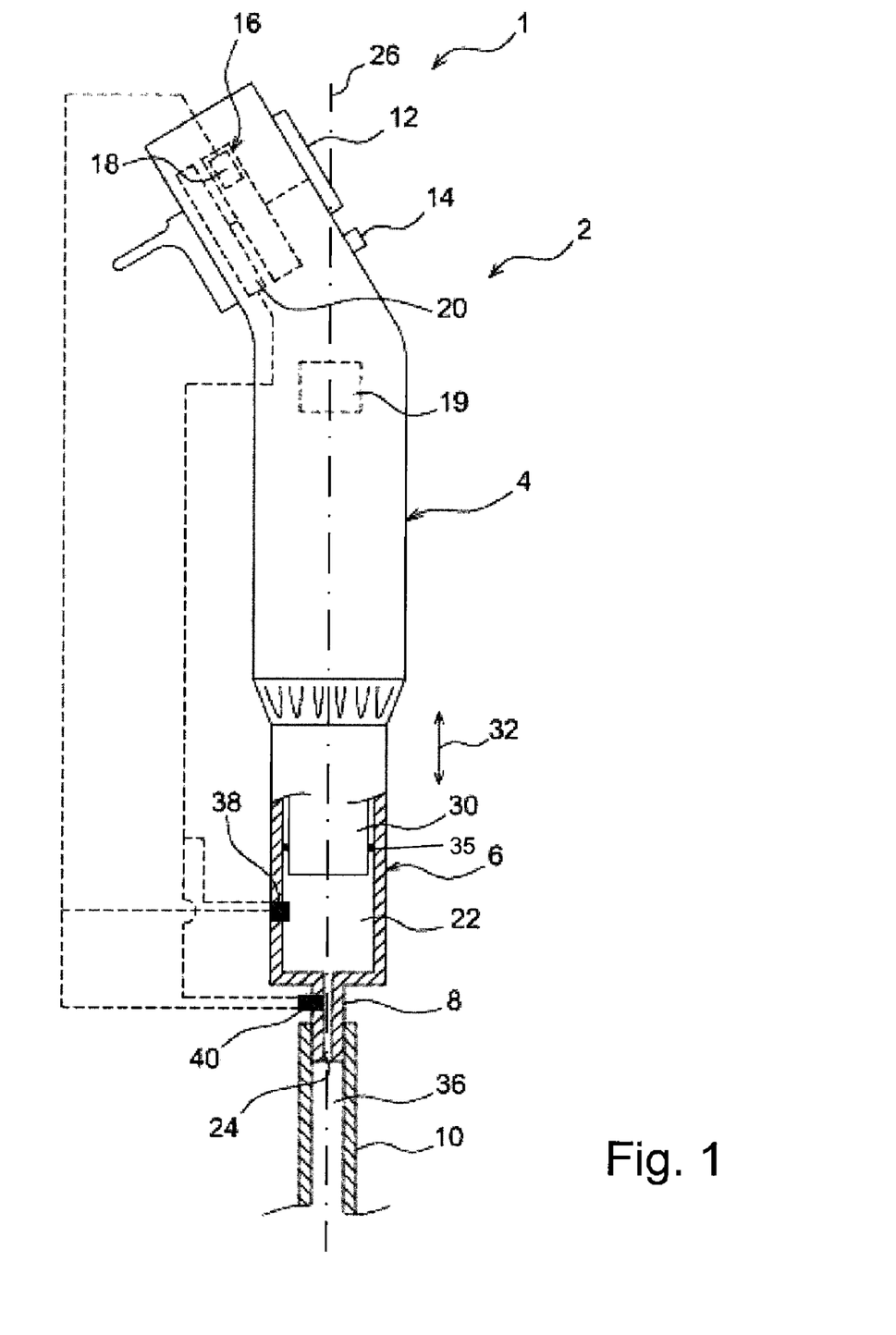
FIG. 1 shows a side view of a viscometer in accordance with an illustrative embodiment.

With reference to FIG. 1, a side view of a viscometer 1 is shown in accordance with an illustrative embodiment. Viscometer 1 is configured to determine a viscosity of a liquid. Viscometer 1 may include a pipette 2 and a tube 10 which mounts to pipette 2. As used herein, the term "mount" includes join, unite, connect, associate, insert, hang, hold, affix, attach, fasten, bind, paste, secure, bolt, screw, rivet, solder, weld, press fit, mold, and other like terms. Tube 10 may be removably mounted to pipette 2, for example, using a press fit. Pipette 2 may comprise a motor driven single channel or multi-channel pipette. Pipette 2 further may be an electronically controlled pipette that may be handheld. Thus, Pipette 2 may be portable and of small size. Any conventional pipette may be modified to form viscometer 1.

Pipette 2 may include a top part 4 and a bottom part 6 which mounts to top part 4. Bottom part 6 may be removably mounted to top part 4, for example, using a threaded nut arrangement. Bottom part 6 may include an end-piece 8 for holding tube 10. For example, tube 10 may be slid onto end-piece 8 in a removable manner. Top part 4 may include a body forming a handle that is held by a user.

Top part 4 may include a display 12, an input device 14, a processor 16, a computer readable medium 18, an actuator 19, and a power supply 20. Display 12 presents information to a user of pipette 2. Input device 14 provides a mechanism for inputting information into pipette 2. Input device 14 may comprise one or more input mechanisms employing various input technologies including, but not limited to, a keyboard, a pen and touch screen, a mouse, a track ball, a touch screen, a keypad, a thumbwheel, a button, etc. to allow the user to enter information into pipette 2 or to make selections from items presented in display 12.

Computer readable medium 18 is an electronic holding place or storage for information so that the information can be accessed by processor 16. Pipette 2 may have one or more computer readable media that use the same or a different memory technology. Memory technologies include, but are not limited to, any type of random access memory (RAM), any type of read only memory, any type of flash memory, etc. Pipette 2 also may have one or more drives that support the loading of a computer readable medium such as a compact disk or digital video disk. Pipette 2 also may have one or more communication interfaces that allow communication with an external device that may include one or more computer readable media.

Processor 16 executes instructions as known to those skilled in the art. The instructions may be carried out by a special purpose computer, logic circuits, or hardware circuits. Thus, processor 16 may be implemented in hardware, firmware, software, or any combination of these methods. The term "execution" is the process of running an application or the carrying out of the operation called for by an instruction. The instructions may be written using one or more programming language, scripting language, assembly language, etc. Processor 16 executes an instruction, meaning that it performs the operations called for by that instruction. Processor 16 operably couples with display 12, with input device 14, with computer readable medium 18, and with any communication interface to receive, to send, and to process information. Processor 16 may retrieve a set of instructions, such as a viscometer application, from a permanent memory device and copy the instructions in an executable form to a temporary memory device that is generally some form of RAM. Pipette 2 may include a plurality of processors that use the same or a different processing technology.

The viscometer application may perform operations associated with determining a viscosity of a liquid. Some or all of the operations and interfaces subsequently described may be embodied in the viscometer application. The operations may be implemented using hardware, firmware, software, or any combination of these methods. The viscometer application may be written using one or more programming languages, assembly languages, scripting languages, etc.

Actuator 19 may be a motor configured to control movement of a control rod under the control of processor 16 and the viscometer application. In an illustrative embodiment, actuator 19 may be implemented using a variety of electromechanical devices as known to those skilled in the art. Power supply 20 may include a battery to provide power to the various components of pipette 2.

Bottom part 6 may include an intake chamber 22 that communicates with an bore 24 of end-piece 8. Bore 24 extends generally parallel to or coincident with a longitudinal axis 26 of pipette 2. Bore 24 has a first end that opens into intake chamber 22 and a second end that opens to an external environment or to tube 10 if mounted to end-piece 8. A piston 30 is mounted to slide within intake chamber 22 in a sliding direction 32 parallel to longitudinal axis 26. In a manner that is known, the movements of piston 30 in sliding direction 32 are controlled, for example using actuator 19, to dispense and aspirate a liquid.

In an illustrative embodiment, tube 10 is formed from glass or plastic and may be disposed after each use. Tube 10 includes a channel 36 through which the liquid is aspirated and dispensed. In an illustrative embodiment, channel 36 includes at least a portion having a constant cross-section, such as a cylindrical portion, that is generally perpendicular to longitudinal axis 26 when mounted to pipette 2. In the example shown in FIG. 1, channel 36 is cylindrical over its entire length, thus forming a single portion of constant cross-section though this is not required. For example, channel 36 may include a bottom end that is conical and in communication with a cylindrical portion. As another example, channel 36 may include a plurality of cylindrical portions having different diameters and connected with a conical section that transitions gradually between different diameters or abruptly changes between different diameters.

Viscometer 1 may further include measurement means. For example, with reference to FIG. 1, viscometer 1 may include a relative pressure sensor 38 mounted inside intake chamber 22, and therefore in the dead volume of pipette 2. Relative pressure sensor 38 is configured to provide data on a value of a pressure P inside intake chamber 22 relative to an atmospheric pressure $P_0$ that exists outside pipette 2. Thus, relative pressure sensor 38 may be configured to monitor the pressure as a function of time as $\Delta P(t)=P_0-P(t)$. Viscometer 1 further may include an absolute pressure sensor 40 mounted, for example, on an outside of end-piece 8 to measure the atmospheric pressure $P_0$. In an alternative embodiment, viscometer 1 may not include relative pressure sensor 38 such that P(t) is measured and used to calculate $\Delta P(t)$ as a function of a plurality of pressure measurements. Absolute pressure sensor 40 may measure the atmospheric pressure $P_0$ when intake chamber 22 is in communication with outside air. If used, relative pressure sensor 38 may be mounted at other locations on or adjacent to pipette 2.

Relative pressure sensor 38 and absolute pressure sensor 40 may be powered electrically by power supply 20 of pipette 2. Relative pressure sensor 38 and absolute pressure sensor 40 further may be connected to send measured data to computer readable medium 18 for access by processor 16 of pipette 2. In another embodiment, the measurement means may be connected to a computer and/or power supply external to pipette 2. Additionally, relative pressure sensor 38 and absolute pressure sensor 40 may be incorporated into top part 4 and connected to bottom part 6 using appropriate conduits.

Figure 2:
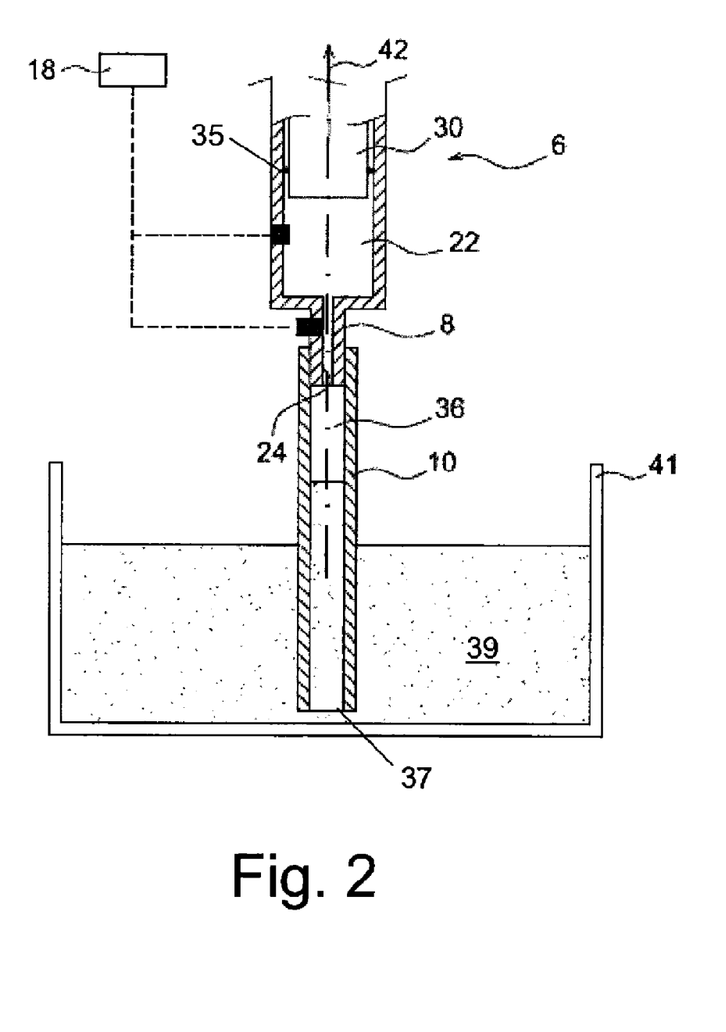
FIG. 2 shows a schematic view of a bottom part of a pipette of the viscometer of FIG. 1 in accordance with a first illustrative embodiment.

Viscometer 1 can be used to determine the viscosity of a Newtonian or non-Newtonian fluid. With reference to FIG. 2, pipette 2 is positioned so that a bottom end 37 of channel 36 of tube 10 is located a few millimeters below the surface of a liquid 39 contained in a receptacle 41. A pipetting operation is initiated using pipette 2, leading to a liquid aspiration performed by the rise of piston 30 in intake chamber 22, as indicated by an arrow 42. During this operation, piston 30 is controlled at a constant speed so that liquid 39 also enters a cylindrical portion of channel 36 of tube 10 at a constant speed.

Simultaneously, relative pressure sensor 38 measures the value of the function ΔP(t)=P$_0$−P(t) and sends the measurements to computer readable medium 18 for access by processor 16 of pipette 2. For example, relative pressure sensor 38 measures a relative pressure value of the function ΔP(t) at a plurality of time instants during aspiration of the liquid in the cylindrical portion of channel 36 of tube 10. To improve the accuracy of the viscosity, the measurement is performed a great many times during the upward stroke of piston 30.

Due to the cylindrical nature of the cylindrical portion of channel 36 of tube 10 and the constant speed of piston 30, the function ΔP(t) is a linear time function of a director coefficient λ, corresponding to a derivative of the function ΔP(t) and thus a slope of ΔP(t). For example, as shown with reference to FIG. 3, λ can be calculated as $$\lambda = \frac{(\Delta P_2 - \Delta P_1)}{(t_2 - t_1)}.$$

Figure 3:
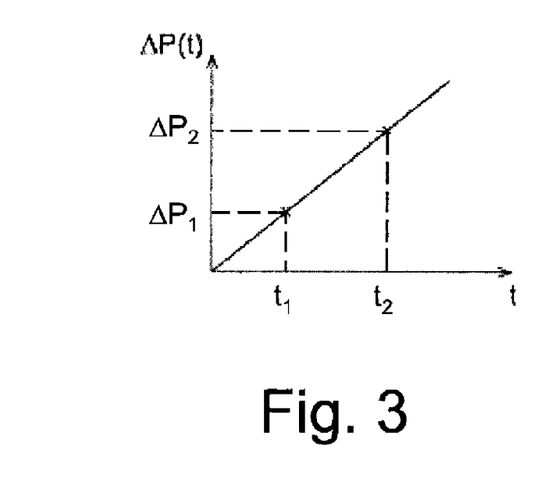
FIG. 3 shows a graph representing the function $\Delta P(t)$ as a function of time during a pipetting operation in accordance with an illustrative embodiment.

Using the plurality of relative pressure values received from relative pressure sensor 38 at different moments in time, processor 16 is configured to determine a value of the director coefficient λ, by any method known to those skilled in the art. For example, processor 16 may execute the viscometer application configured to perform the operations associated with the calculation of the value of the director coefficient λ or of the director coefficient −λ.

The determined value of the director coefficient λ may be used in equation (1) to determine the viscosity η of liquid 39 with a high degree of precision $$\eta = \frac{d^2}{32k^2}\left[\frac{P_0}{V_0}q_P - \left(\frac{P_0}{V_0}\frac{\pi d^2}{4} + \rho g\right)k\right] \quad (1)$$

where $$k = \left(q_P - \frac{V_0 \lambda}{P_0}\right)\frac{4}{\pi d^2}, \quad q_P$$

is the volume swept by piston 30 per time unit and is equal to the product of the speed of piston 30 multiplied by a cross section of piston 30 relative to longitudinal axis 26, d is the diameter of the cylindrical portion of channel 36 of tube 10, ρ is the density of liquid 39, g is the acceleration of gravity, V$_0$ is the dead volume of pipette 2 at time t=0 of the measurement, P$_0$ is the atmospheric pressure.

Viscometer 1 can be adapted to the nature of liquid 39. For example, a tube 10 may be selected from a plurality of tubes having different diameters, and/or a piston 30 may be selected from a plurality of pistons having different diameters, and/or actuator 19 may be used to control the speed of piston 30 to operate at different speeds that are constant during different phases; and/or the dead volume of pipette 2 may be adjusted. By increasing the diameter of channel 36, liquids of higher viscosity can be tested and vice versa. A plurality of interchangeable bottom parts of pipette 2 may be used to select different piston diameters. An increase in the diameter of piston 30 increases the volume swept by piston 30 leading to an increase in the shear rate of liquid 39, thus providing access to the measurement of lower viscosities. Moreover, pistons of larger diameter are generally associated with tubes that have a large passage diameter to ensure that they will be filled and to effect a more effective purging of the viscous liquids. Alternatively, the choice of piston diameter can be provided using a multistage piston. By increasing the speed of piston 30, the shear rate of liquid 39 is increased, and therefore the amplitude of the viscous forces so that liquids having a low viscosity can be measured. Low piston speeds are preferred so that the flow of liquid 39 in tube 10 remains laminar and the measurement does not include hydraulic pressure drops resulting from a turbulent flow.

To support this adaptability, bottom part 6 may be removable and replaceable to support different tube sizes and/or shapes and/or including a different diameter piston. Alternatively, with reference to the illustrative embodiment of FIG. 4, piston 30 may comprise a multi-stage piston such as those described in U.S. patent application Ser. No. 11/619,882 assigned to the assignee of the present application and incorporated herein by reference in its entirety. In the illustrative embodiment of FIG. 4, piston 30 includes several sections of different diameter, respectively mating with intake chambers connected together by one or more electro-valves 46. The lowest, intake chamber 22, communicates with end-piece 8. The user can control the electro-valves 46 to select the desired piston diameter.

In order to get a precise value of λ, and therefore of the fluid viscosity, it is desirable to have a small dead volume, where the dead volume can be defined by the sum of the volumes of channel 36 of tube 10, of the fluid communication means between relative pressure sensor 38 and intake chamber 22, of bore 24 of end-piece 8, and of intake chamber 22 extending to a sealing ring 35 surrounding piston 30. In an illustrative embodiment, a small dead volume is used to improve the accuracy in determining the viscosity, because the lower the dead volume, the greater the vacuum in intake chamber 22, and therefore the steeper the slope of the function ΔP(t) and more easily determinable. Of the parameters indicated above that can be modified by the user, the diameter of piston 30 as well as the diameter of channel 36 of tube 10 have a direct influence on the dead volume.

Figure 5:
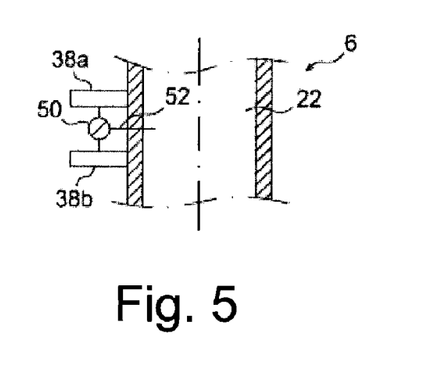
FIG. 5 shows a partial schematic view of the bottom part of the pipette of the viscometer of FIG. 1 in accordance with a third illustrative embodiment.

Nevertheless, a small dead volume can result in a high pressure in intake chamber 22, which may not be acceptable for relative pressure sensor 38. To overcome this possible issue, a first alternative embodiment, illustrated in FIG. 5 may be used. With reference to the illustrative embodiment of FIG. 5, relative pressure sensor 38 is replaced by a first sensor 38a and a second sensor 38b. First sensor 38a and second sensor 38b have different sensitivity ranges such that each is capable of determining the value of ΔP(t) over a different pressure range. The different pressure ranges may overlap. First sensor 38a and second sensor 38b are connected together so that second sensor 38b with the lowest sensitivity range automatically performs the pressure measurement when the pressure measured by first sensor 38a of higher sensitivity range attains a threshold that is predetermined and may be close to the saturation pressure of first sensor 38a. For example, an electro-valve 50 may be used that communicates first with intake chamber 22 via a conduit 52, and second, alternatively with each of first sensor 38a and second sensor 38b. Thus, as long as the pressure does not exceed the aforementioned threshold, first sensor 38a having a higher sensitivity range than second sensor 38b remains in operation, and sends a measurement of the value ΔP(t) to computer readable medium 18 for access by processor 16 of pipette 2. At any instant t' of the measurement at which the pressure attains the predetermined threshold, the electro-valve 50 switches automatically to bring into operation second sensor 38b having a lower sensitivity range than first sensor 38a.

Figure 6:
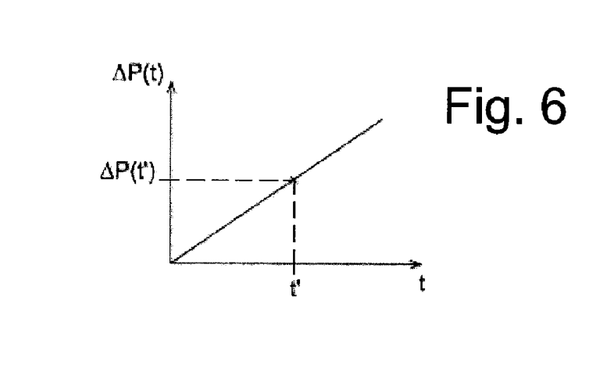
FIG. 6 shows a graph representing the function $\Delta P(t)$ as a function of time during a pipetting operation using the bottom part of the pipette of the viscometer of FIG. 5 in accordance with an illustrative embodiment.

As shown with reference to FIG. 6, the graph of the value of ΔP(t) retains the form of a straight line with slope λ, even in the event of switching during the measurement. Thus, the values for determining the slope λ can be taken before and/or after the instant of switching t'.

Figure 7:
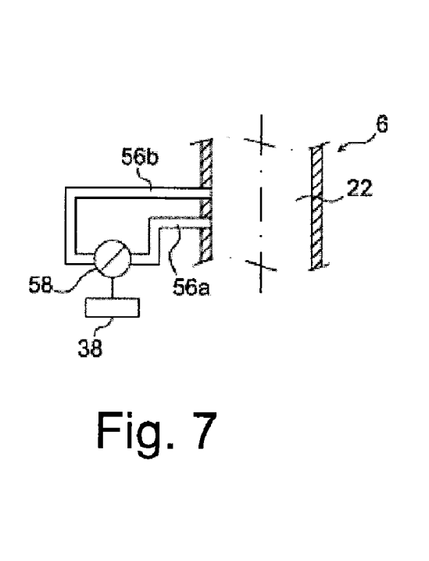
FIG. 7 shows a partial schematic view of the bottom part of the pipette of the viscometer of FIG. 1 in accordance with a fourth illustrative embodiment.
Figure 8:
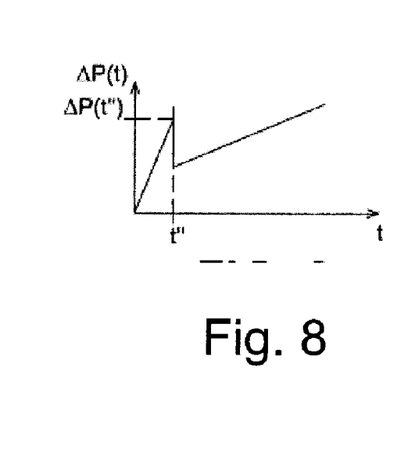
FIG. 8 shows a graph representing the function $\Delta P(t)$ as a function of time during a pipetting operation using the bottom part of the pipette of the viscometer of FIG. 7 in accordance with an illustrative embodiment.

Alternatively, it is possible to provide a small dead volume in order to obtain good measurement accuracy, and to retain the ability to increase it during the measurement, in the event of excessive pressure in intake chamber 22. To this end, a second alternative embodiment, shown in FIG. 7, indicates that relative pressure sensor 38 is connected to intake chamber 22 by a first conduit 56a and a second conduit 56b having different diameters. For example, as shown in the illustrative embodiment of FIG. 7, first conduit 56a has a smaller diameter than second conduit 56b. An electro-valve 58 is connected to relative pressure sensor 38 and alternatively to first conduit 56a and second conduit 56b that communicate with intake chamber 22. By default, communication between relative pressure sensor 38 and intake chamber 22 may be effected using first conduit 56a having the smaller diameter conduit to result in a small dead volume and providing a high measurement accuracy. In the event of excessive pressure in intake chamber 22, electro-valve 58 switches automatically to change the communication between relative pressure sensor 38 and intake chamber 22 to use second conduit 56b having a larger diameter. At this moment t'', the result is a pressure drop in intake chamber 22, and therefore a different slope λ, as illustrated by the graph of FIG. 8. The slope λ obtained after the time instant t'' is chosen by processor 16 of pipette 2 for determining the value λ. Here again, the commutation can be effected by comparing the measured pressure to a saturation pressure of relative pressure sensor 38.

Figure 4:
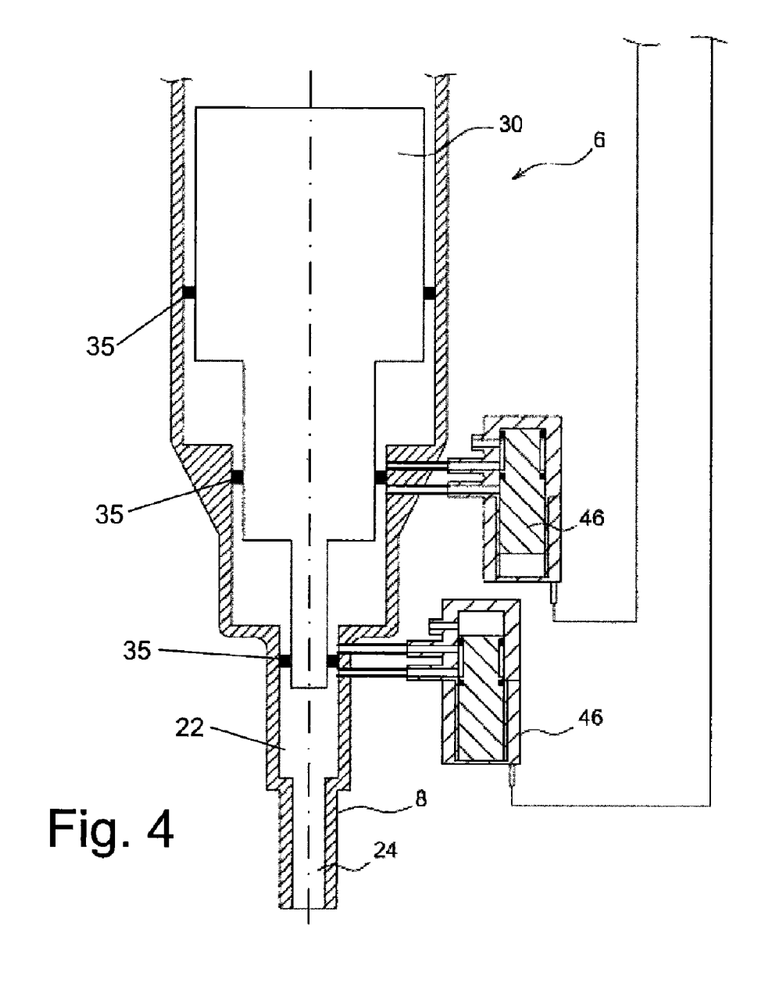
FIG. 4 shows a schematic view of the bottom part of the pipette of the viscometer of FIG. 1 in accordance with a second illustrative embodiment.

Other methods can be used to modify the dead volume during the measurement, such as a change of piston, using a multi-stage piston as shown in FIG. 4, etc.

Figure 9:
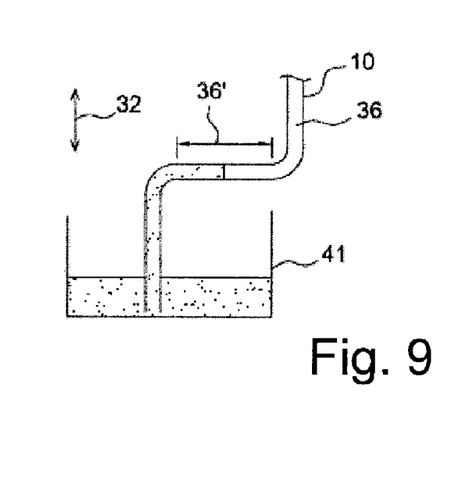
FIG. 9 shows a schematic view of a tube of the viscometer of FIG. 1 in accordance with a second illustrative embodiment.

As indicated in equation (1), the value of the viscosity depends on the density ρ of liquid 39 which may be stored in computer readable medium 18 initially and/or entered by the user. With reference to FIG. 9, if ρ is unknown, channel 36 tube 10 may be configured to include a cylindrical and a horizontal portion 36'. Horizontal portion 36' is generally orthogonal to sliding direction 32 of piston 30. Using this configuration, when liquid 39 transits in the horizontal portion of constant section 36', the pressure ΔP(t) results only from the fluid viscosity, and is no longer sensitive to the hydrostatic pressure which depends on the density of the fluid, as can be the case for example during the rise of the liquid in the vertical bottom part of tube 10. Thus, the signal ΔP(t) only takes account of the viscous component. As a result, to determine the liquid viscosity using equation (1), the value of ρ is set to zero.

As another example, the density ρ of liquid 39 can be determined using equation (2) below by measuring the hydrostatic pressure in intake chamber 22 at the end of a pipetting operation when channel 36 contains a liquid column of height h, when piston 30 is immobile, and when the change in pressure ΔP has stabilized.

$$\rho = \frac{\Delta P}{gh} \quad (2)$$

For Newtonian fluids, another option depends on the ability to perform two tests in separate experimental conditions, to deduce the value of λ for each of the two tests, and to solve the system of two equations each derived from equation (1), where the two unknown parameters to be determined are η and ρ. The solution of is obtained by equating the two equations, given that the Newtonian character of liquid 39 means that the viscosity is the same irrespective of the experimental conditions. In this regard, the experimental conditions can be modified between the two tests by modifying the diameter of the cylindrical portion of channel 36, and/or the speed of piston 30, and/or the diameter of piston 30, and/or by any other modification of the dead volume.

Figure 10:
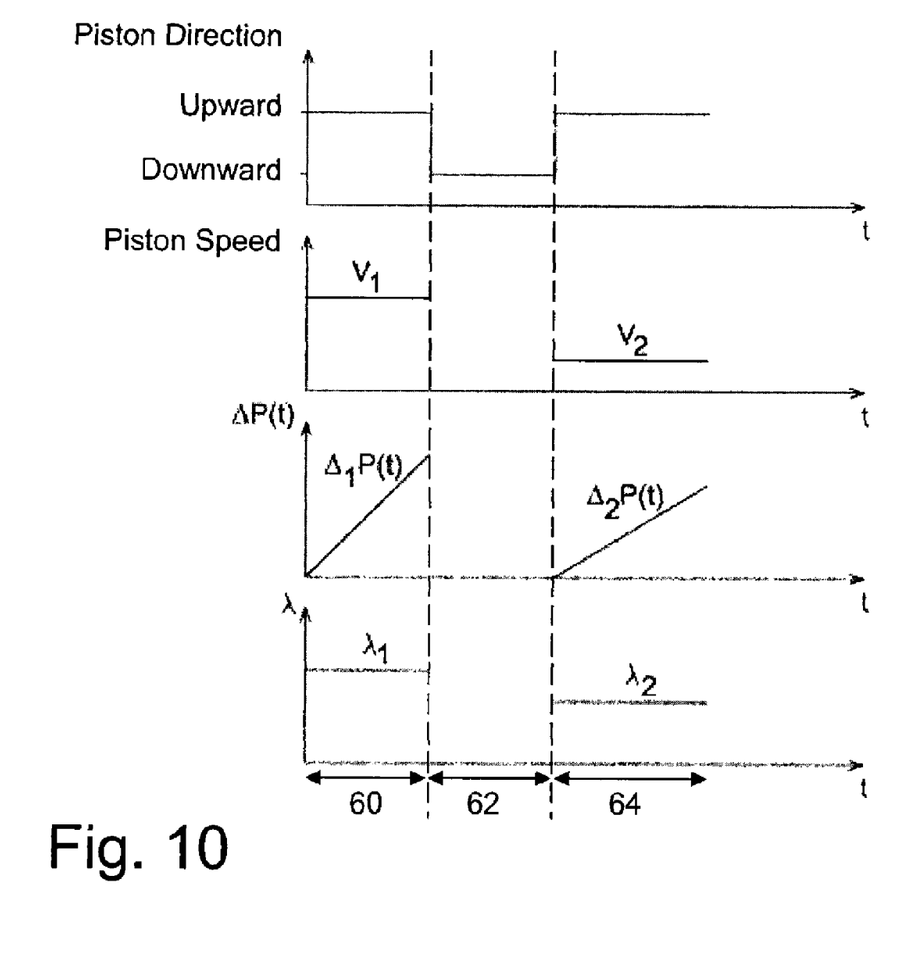
FIG. 10 includes a series of graphs relating to different phases using the viscometer of FIG. 1 to determine the viscosity of a Newtonian liquid in accordance with an illustrative embodiment.

With reference to FIG. 10, an illustrative embodiment is shown for conducting separate experiments to deduce the value of λ and to solve the system of two equations derived from equation (1) for the two unknown parameters η and ρ. Measurement of the value of ΔP(t) during each of two successive intake strokes keeping liquid 39 in channel 36 is performed using a first upward stroke, a downward stroke, and a second upward stroke designed for intake of liquid 39, all by keeping liquid 39 in channel 36 but, for example, reducing the speed of piston 30 during the second upward stroke. In the illustrative embodiment of FIG. 10, a first phase 60 over a first time window is associated with a first upward stroke of piston 30 implemented with a given piston speed $V_1$, which generates a rising straight line $\Delta_1 P(t)$, leading to a value $\lambda_1$, which itself is linked to the viscosity η by equation (1). In a second phase 62 over a second time window, a downward stroke of piston 30 results in dispensing of liquid 39 located in channel 36. In an illustrative embodiment, no measurement is taken during second phase 62. In a third phase 64 over a third time window, while liquid 39 remains present in a small quantity in channel 36, a second upward stroke of piston 30 is performed at a speed $V_2$, for example reduced by half in relation to the speed $V_1$, which generates a straight line $\Delta_2 P(t)$, leading to a value $\lambda_2$, itself linked to the viscosity η by equation (1). Equating the two equations leads to a determination of the viscosity η and of the density ρ.

The process illustrated in FIG. 10 may be performed any number of times. Thus, when the atmospheric pressure $P_0$ is not determined, for example, if absolute pressure sensor 40 is not used, a third upward stroke of piston 30 in conditions that are different from those of the first and second upward strokes can be used to solve the system of three equations derived from equation (1), where the three unknown parameters to be determined are then η, ρ, and $P_0$.

More generally, for a Newtonian liquid, the value of λ for a number N of distinct experimental conditions strictly greater than one can be used to determine the value of each of a number N'=N−1 parameters that are also unknown, in addition to the viscosity. Thus, for example, determining the viscosity and the N−1 other unknown parameters can be effected by resolution of a system of N equations with N unknowns, each established using equation (1) completed by the data relating to the particular experimental conditions applied.

Figure 11:
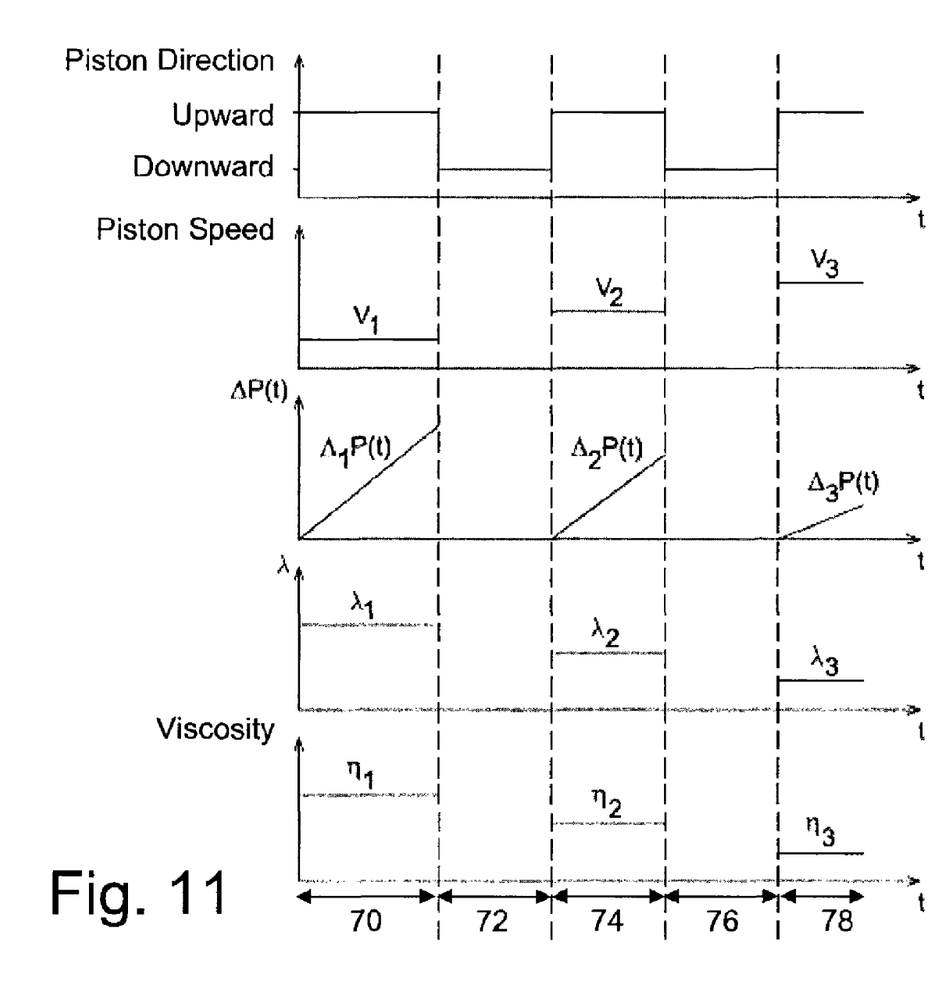
FIG. 11 includes a series of graphs relating to different phases using the viscometer of FIG. 1 to determine the viscosity of a non-Newtonian liquid for different rates of shear in accordance with an illustrative embodiment.

As a result of the ability to effect measurements during successive upward stroke phases, the rheogram of a non-Newtonian liquid, namely the shear value can be determined. With reference to FIG. 11, an illustrative method is shown in which the shear rate is modified at each new upward stroke of piston 30 by applying a corresponding piston speed. A first phase 70 is associated with a first upward stroke of piston 30 implemented with a given piston speed $V_1$, which generates a rising straight line $\Delta_1 P(t)$, leading to a value $\lambda_1$, which itself is linked to the viscosity $\eta_1$ by equation (1), for the shear rate concerned. In a second phase 72, a first downward stroke of piston 30 results in dispensing of liquid 39 located in channel 36. In an illustrative embodiment, no measurement is taken during second phase 72. In a third phase 74, while liquid 39 remains present in a small quantity in channel 36, a second upward stroke of piston 30 is performed at a speed $V_2$, for example doubled in relation to the speed $V_1$, which generates a straight line $\Delta_2 P(t)$, leading to a value $\lambda_2$, itself linked to the viscosity $\eta_2$ by equation (1), for the new shear rate concerned. In a fourth phase 76, a second downward stroke of piston 30 results in dispensing of liquid 39 located in channel 36. In an illustrative embodiment, no measurement is taken during fourth phase 76. In a fifth phase 78, while liquid 39 remains present in a small quantity in channel 36, a third upward stroke of piston 30 is performed at a speed $V_3$, for example doubled in relation to the speed $V_2$, which generates a straight line $\Delta_3 P(t)$, leading to a value $\lambda_3$, itself linked to the viscosity $\eta_3$ by equation (1), for the new shear rate concerned. The method can be continued in this way as many times as needed, by keeping liquid 39 within channel 36 of tube 10.

According to another alternative embodiment, the speed of flow of liquid 39 can be modified during a given intake stroke of piston 30, during which several measurements of the slope of the function $\Delta P(t)$ or of the function $P(t)$ are obtained to determine the viscosity for different shear rates. The speed of liquid 39, and therefore the shear rate of liquid 39, can be modified automatically by arranging that liquid 39 transits successively via cylindrical staged portions of channel 36 of different diameter, arranged within tube 10. The viscosity for both non-Newtonian liquids and Newtonian liquids can be determined using this method.

The viscosity of a non-Newtonian liquid can be calculated for different rates of shear by varying the speed of flow of liquid 39 within the cylindrical portion of channel 36. The various phases are performed one after the other by filling and then completely emptying tube 10 after each phase where each phase applies a given speed of flow to the liquid, itself corresponding to a given shear rate. The parameters to vary the speed of the liquid include the speed of piston 30, and/or the diameter of tube 10, and/or the diameter of piston 30.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system for determining a viscosity of a fluid, the system comprising:
    an intake chamber;
    a tube in communication with the intake chamber and comprising a channel, wherein the channel includes a cylindrical portion having a constant diameter cross section;
    a piston mounted in the intake chamber;
    an actuator configured to move the piston within the intake chamber at a constant speed during a time window to aspirate a fluid in the cylindrical portion of the channel;
    a sensor configured to measure a pressure a plurality of times during the time window to define a plurality of pressure measurements; and
    a processor configured to receive the defined plurality of pressure measurements, to determine a slope associated with the received plurality of pressure measurements, and to determine a viscosity of the fluid based on the determined slope;
    wherein the measured pressure is an absolute pressure.

2. The system of claim 1, wherein the cylindrical portion is generally perpendicular to a direction of movement of the piston.

3. The system of claim 1, wherein the cylindrical portion is generally parallel to a direction of movement of the piston.

4. The system of claim 1, wherein the slope is determined using a plurality of relative pressure measurements calculated from the plurality of absolute pressure measurements.

5. The system of claim 1, wherein the viscosity is calculated based on $$\eta = \frac{d^2}{32k^2}\left[\frac{P_0}{V_0}q_P - \left(\frac{P_0}{V_0}\frac{\pi d^2}{4} + \rho g\right)k\right] \text{ where}$$

where $$k = \left(q_P - \frac{V_0 \lambda}{P_0}\right)\frac{4}{\pi d^2}, q_P$$

is a volume swept by the piston per time unit, d is a diameter of the cylindrical portion, $\rho$ is a density of the liquid, g is an acceleration of gravity, $V_o$ is a dead volume of the tube and the intake chamber, $P_o$ is an atmospheric pressure, and l is the determined slope.

6. The system of claim 1, wherein the processor is further configured to control a speed of the actuator.

7. The system of claim 1, wherein the piston is a multi-stage piston.

8. The system of claim 1, wherein the sensor comprises a first sensor configured to measure a relative pressure and a second sensor configured to measure the absolute pressure.

9. The system of claim 1, further comprising an end-piece comprising a bore providing communication between the intake chamber and the channel.

10. The system of claim 1, wherein the sensor comprises a first sensor configured to measure a first pressure with a first sensitivity range and a second sensor configured to measure a second pressure with a second sensitivity range, wherein the first sensitivity range is lower than the second sensitivity range.

11. The system of claim 1, further comprising an electro-valve connected between the intake chamber and the sensor by a first conduit and by a second conduit, wherein the first conduit has a different diameter than the second conduit, and further wherein the electro-valve is configured to switch between the first conduit and the second conduit based on the measured pressure.

12. The system of claim 1, wherein the intake chamber, the piston, and the actuator are mounted in a pipette and further wherein the sensor is mounted to a housing of the pipette.

13. The system of claim 8, wherein the first sensor is mounted to the intake chamber to measure a pressure within the intake chamber.

14. The system of claim 9, wherein the tube removably mounts to the end-piece.

15. The system of claim 10, further comprising an electro-valve connected between the intake chamber, the first sensor, and the second sensor, wherein the electro-valve is configured to automatically switch the connection with the intake chamber from the first sensor to the second sensor based on the measured pressure, the first sensitivity range, and the second sensitivity range.

16. The system of claim 12, wherein the processor is further mounted in the pipette.

17. The system of claim 16, wherein the pipette is hand-held.

18. A system for determining a viscosity of a fluid, the system comprising:
   an intake chamber;
   a tube in communication with the intake chamber and comprising a channel, wherein the channel includes a cylindrical portion having a constant diameter cross section;
   a piston mounted in the intake chamber;
   an actuator configured to move the piston within the intake chamber at a constant speed during a time window to aspirate a fluid in the cylindrical portion of the channel;
   a sensor configured to measure a pressure a plurality of times during the time window to define a plurality of pressure measurements; and
   a processor configured to receive the defined plurality of pressure measurements, to determine a slope associated with the received plurality of pressure measurements, and to determine a viscosity of the fluid based on the determined slope;
   wherein the measured pressure is a relative pressure.

19. The system of claim 18, wherein the cylindrical portion is generally perpendicular to a direction of movement of the piston.

20. The system of claim 18, wherein the cylindrical portion is generally parallel to a direction of movement of the piston.

21. The system of claim 18, wherein the processor is further configured to control a speed of the actuator.

22. The system of claim 18, further comprising an electro-valve connected between the intake chamber and the sensor by a first conduit and by a second conduit, wherein the first conduit has a different diameter than the second conduit, and further wherein the electro-valve is configured to switch between the first conduit and the second conduit based on the measured pressure.

23. The system of claim 18, further comprising an end-piece comprising a bore providing communication between the intake chamber and the channel.

* * * * *